US007935312B2

(12) United States Patent
Northrup et al.

(10) Patent No.: US 7,935,312 B2
(45) Date of Patent: *May 3, 2011

(54) MICROFABRICATED REACTOR, PROCESS FOR MANUFACTURING THE REACTOR, AND METHOD OF AMPLIFICATION

(75) Inventors: M. Allen Northrup, Berkeley, CA (US); Richard M. White, Berkeley, CA (US)

(73) Assignee: Regents of the University of California, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/471,718

(22) Filed: Jun. 21, 2006

(65) Prior Publication Data

US 2007/0117111 A1    May 24, 2007

Related U.S. Application Data

(63) Continuation of application No. 08/482,933, filed on Jun. 6, 1995, now Pat. No. 7,297,313, which is a continuation of application No. 07/938,106, filed on Aug. 31, 1992, now Pat. No. 5,639,423.

(51) Int. Cl.
*C12M 1/34* (2006.01)

(52) U.S. Cl. ......... 422/138; 422/67; 422/68.1; 422/131; 435/287.2

(58) Field of Classification Search .................... 422/50, 422/68.1, 81, 105–116, 129, 198, 63–65, 422/102, 131, 138; 435/6, 7.9, 287.2, 287.3, 435/283.1, 289.1
See application file for complete search history.

(56) References Cited

U.S. PATENT DOCUMENTS

| | | | |
|---|---|---|---|
| 2,127,193 A | 8/1938 | Toulmin, Jr. | |
| 3,029,743 A | 4/1962 | Johns | |
| 4,219,335 A | 8/1980 | Ebersole | |
| 4,368,423 A * | 1/1983 | Liburdy | 324/692 |
| 4,556,467 A | 12/1985 | Kuhn et al. | |
| 4,596,697 A | 6/1986 | Ballato | |
| 4,598,049 A | 7/1986 | Zelinka et al. | |
| 4,602,184 A | 7/1986 | Meitzler | |
| 4,632,808 A | 12/1986 | Yamamoto et al. | |
| 4,673,657 A | 6/1987 | Christian | |
| 4,676,274 A | 6/1987 | Brown | |

(Continued)

FOREIGN PATENT DOCUMENTS

DE    3811052 C1    8/1989

(Continued)

OTHER PUBLICATIONS

Esashi, et al., "Integrated Flow Control Systems Fabricated on a Silicon Wafer," Proceedings Electrochemical Society Conf. III, Oct. 18-23, 1987, pp. 31-38B.

(Continued)

*Primary Examiner* — Jill Warden
*Assistant Examiner* — Cedric Chan
(74) *Attorney, Agent, or Firm* — Cooley LLP

(57) ABSTRACT

An integrated microfabricated instrument for manipulation, reaction and detection of microliter to picoliter samples. The instrument is suited for biochemical reactions, particularly DNA-based reactions such as the polymerase chain reaction, that require thermal cycling since the inherently small size of the instrument facilitates rapid cycle times. The integrated nature of the instrument provides accurate, contamination-free processing. The instrument may include reagent reservoirs, agitators and mixers, heaters, pumps, and optical or electromechanical sensors. Ultrasonic Lamb-wave devices may be used as sensors, pumps and agitators.

18 Claims, 8 Drawing Sheets

U.S. PATENT DOCUMENTS

| | | | |
|---|---|---|---|
| 4,683,195 A | | 7/1987 | Mullis et al. |
| 4,692,654 A | | 9/1987 | Umemura et al. |
| 4,708,931 A | | 11/1987 | Christian |
| 4,737,464 A | | 4/1988 | McConnell et al. |
| 4,759,828 A | | 7/1988 | Young et al. |
| 4,908,112 A | * | 3/1990 | Pace .......................... 210/198.2 |
| 4,920,056 A | | 4/1990 | Dasgupta |
| 4,952,266 A | | 8/1990 | Tsuruta et al. |
| 4,960,486 A | | 10/1990 | Perkins et al. |
| 4,963,498 A | | 10/1990 | Hillman et al. |
| 5,000,817 A | | 3/1991 | Aine |
| 5,003,822 A | | 4/1991 | Joshi |
| 5,006,749 A | | 4/1991 | White |
| 5,129,261 A | | 7/1992 | Riley |
| 5,129,262 A | | 7/1992 | White et al. |
| 5,153,476 A | | 10/1992 | Kosinski |
| 5,187,083 A | * | 2/1993 | Mullis .......................... 435/91.1 |
| 5,212,988 A | | 5/1993 | White et al. |
| 5,220,189 A | | 6/1993 | Higashi et al. |
| 5,229,297 A | | 7/1993 | Schnipelsky et al. |
| 5,252,294 A | | 10/1993 | Kroy et al. |
| 5,270,183 A | | 12/1993 | Corbett et al. |
| 5,296,375 A | | 3/1994 | Kricka et al. |
| 5,304,487 A | | 4/1994 | Wilding et al. |
| 5,384,029 A | | 1/1995 | Campbell |
| 5,385,709 A | | 1/1995 | Wise et al. |
| 5,427,946 A | | 6/1995 | Kricka et al. |
| 5,486,335 A | | 1/1996 | Wilding et al. |
| 5,498,392 A | * | 3/1996 | Wilding et al. .............. 422/68.1 |
| 5,639,423 A | | 6/1997 | Northrup et al. |
| 5,646,039 A | | 7/1997 | Northrup et al. |
| 5,674,742 A | | 10/1997 | Northrup et al. |
| 7,169,601 B1 | | 1/2007 | Northrup et al. |
| 7,297,313 B1 | | 11/2007 | Northrup et al. |

FOREIGN PATENT DOCUMENTS

| | | | |
|---|---|---|---|
| EP | 0402995 A2 | | 2/1990 |
| EP | 0385964 A2 | | 9/1990 |
| EP | 0483117 A2 | | 4/1992 |
| EP | 0381501 B1 | | 6/1994 |
| FR | 2650657 A1 | | 2/1991 |
| JP | 62151174 A | * | 7/1987 |
| JP | 1-280694 A | | 11/1989 |
| JP | 5-317030 | | 12/1993 |
| JP | 6-50974 | | 2/1994 |
| JP | 7-506258 | | 7/1995 |
| SU | 1721311 A1 | | 3/1992 |
| WO | WO 91/16966 | | 11/1991 |
| WO | WO 93/22058 | | 11/1993 |
| WO | WO 94/05414 | | 3/1994 |

OTHER PUBLICATIONS

Masuda, et al., "Novel Method of Cell Fusion in a Fluid Constriction Area in Fluid Integrated Circuit," Proc. IEEE/IAS Meeting (1987), pp. 1549-1553.

Pfahler et al, "Liquid Transport in Micron & Submicron Channels", *Sensors & Actuators*, (1990), pp. 431-434.

Backman, Keith, "Ligase Chain Reaction: Diagnostic Tech-nology for the 1990s and Beyond," *Clinical Chemistry*, (1992) vol. 38, No. 3, pp. 457-458.

Erlich, Henry A., ed., "PCR Technology, Principles and Applications for DNA Amplification," *PCR Technology* M Stockton Press, (1989) pp. 32-38.

Fromberz, Peter, et al., "Core-coat conductor of lipid bilayer and micromachined, silicon," *Biochemica et Biophysica Acta*. (1991) vol. 1062, pp. 103-107.

Higuchi, Russel, et al., "Simultaneous Amplification and Detection of Specific DNA Sequences," *Biotechnology*, (Apr. 1992), vol. 10, pp. 413-417.

Hoopman, Timothy L., "Microchanneled Structures,", *Microstructures, Sensors and Actuators*, (1990) Cho, et al. Eds. The American Society of Mechanical Engineers (4 pages).

Howe, Roger T., et al., "Resonant-Mierobridge Vapor Sensor," *IEEE Transactions on Electron Devices*, ED33:499-506 (1986).

Kawasaki, Ernest S., "Sample Preparation from Blood, Cells, and Other Fluids," *PCR Protocols, A Guide to Methods and Applications*, (1990) Innis, Michael A., et al., ed., Academic Press, Inc., Chapter 18, pp. 146-149.

Kricka, et al., "Liquid Transport in Micron and Submicron Channels," *SPIK*, 1167:159-168 (1989).

Mandenius, Carl Fredrik, et al., "The Interaction of Proteins and Cells with Affinity Ligands Covalently Coupled to Silicon Surfaces as Monitored by Ellipsometry," *Analytical Biochemistry*, (1984) vol. 137, pp. 106-114.

Manz, A., et al., "Micromachining of monocrystalline silicon and glass for chemical analysis systems," *Trends in Analytical Chemistry*, (1991) vol. 10. No, 5, pp. 144-149.

Oste, Christian, "Polymerase Chain Reaction," *BioTechniques*, (1988) vol. 6, pp. 162-167.

Parce, J. Wallace, et al., "Detection of Cell-Affecting Agents with a Silicon Biosensor," *Science*, (Oct. 13, 1989) vol. 24, pp. 243-247.

Sato, Kazin, et al. "Individual and Mass Operation of Biological Cells using Micromechanical Silicon Devices," *Sensors and Actuators*, (1990) A21-A23:948-953.

Shoji, Shuichi, et al. "Prototype Miniature Blood Gas Analyser Fabricated on a Silicon Wafer," *Sensors and Actuators* (1988), vol. 15 pp. 101-107.

Van Lintel., H.T.G., et al., "A Piezoelectric Micropump Based on Micromachining of Silicon," *Sensors and Actuators*, 15 (1988)pp. 153-167.

Vossen, John L., et al. "Thin Film Processes," Copyright 1978 Academic Press, Inc., Chapter 1-1, p. 5 and Chapter m-2, p. 309.

Washizu, Masao, et al., "Handling of Biological Cells Using Fluid lntegrated Circuit," *Proceedings IEE/IAS Meeting*, (1988) pp. 1735-1740.

Whitesides, George M., "Molecular Self-Assembly and Nanochemistry: A Chemical Strategy for the Synthesis of Nanostructures," *Science*, vol. 254, pp. 1312-1342.

Andle, J. et al., "Detection of Nucleic Acid Hybridization with an Acoustic Plate Mode Microsensor," *IEEE Ultrasonics Symposium*, vol. 1, Honolulu, Hawaii, Dec. 4-7, 1990, pp, 291-294.

Angell, J.B. et al., "Silicon Micromechanical Devices", *Scientific American*, vol. 248, No. 4, Apr. 1983, pp. 44-55.

Howe, R.T. et al., "Silicon Micromechanics: Sensors and Actuators on a Chip", *IEEE Spectrum*, Jul. 1990, pp. 29-35.

Wenzel, S.T. et al., "A Multisensor Employing an Ultrasonic Lamb—Wave Oscillator", *IEEE Transactions on Electron Devices*, vol. 35, No. 6, Jun. 1988, pp. 735-743.

Wise, K. et al., "Microfabrication Techniques for Integrated Sensors and Microsystems", *Science*, vol. 254, Nov. 29, 1991, pp. 1335-1342.

Wittwer, C. et al., "Minimizing the Time Required for DNA Amplicication by Efficient Heat Transfer to Small Samples", *Analytical Biochemistry*, 186, 1990, pp. 328-331.

Gibbs, R. "DNA Amplification by the Polymerase Chain Reaction", *Analytical Chemistry*, vol. 62, No. 13, Jul. 1, 1990, pp. 1202-1214.

Heller, M. J., et al., "An Efficient Method for Extraction of DNA from Formalin-Fixed, Paraflin-Embedded Tissue by Sonication," *BioTechniques*, (1991) Research Report, vol. 11. No. 3, pp. 372-374 and 476-377.

White, R., U.S. Appl. No, 07/162,193, Feb. 29, 1988 (abandoned).

Hafeman et al.,*Science*, vol. 240, pp. 1182-1185, 1988.

Senturia, Stephen D., et al., Section 2,5; Microprocessor Packaging, (Paper presented at the 14th Automotive Materials Conference, Ann Arbor, MI, U.S.A. Nov. 19, 1986, pp. 185-191.) Reprinted with permission from *Sensors and Actuators*, vol. 15, pp. 221-234, Nov. 1988.

Sundaram, Mani, et al, "New Quantum Structures," *Science*, Nov. 29, 1991, vol. 254, pp. 1326-1335.

Muller et al., Microsensors, *IEEE Press*, 1990 [Book 472 pgs.].

Delphion Report of JP 1-280694A2, Hiroshi et al., Piezoelectric Vibrator Pump Device, dated Feb. 20, 2009, 2 pages.

Dialog Report of SU 1721311A1, Milovanov et al., Vibration Pump, dated Feb. 20, 2009, 3 pages.

* cited by examiner

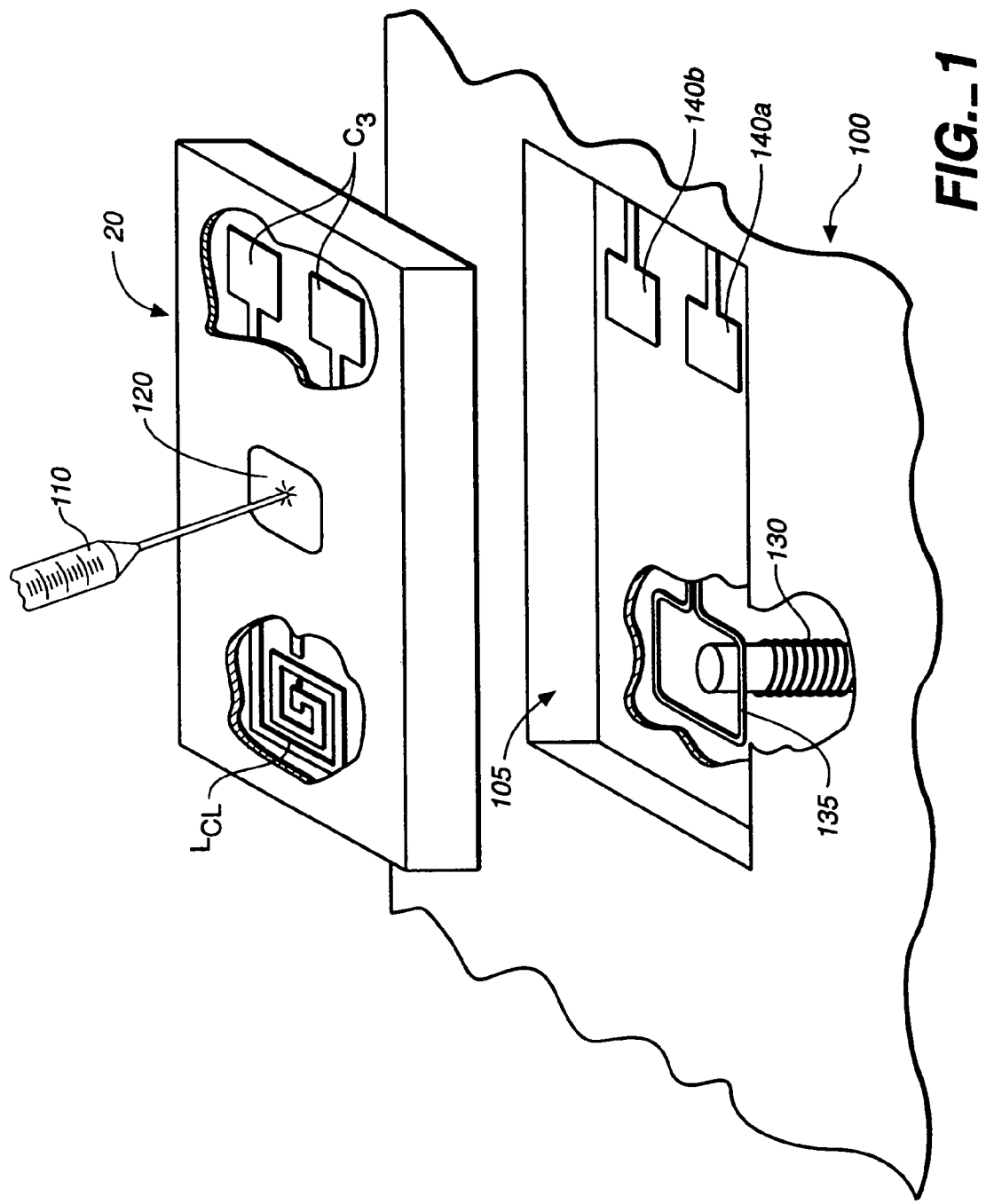
FIG._1

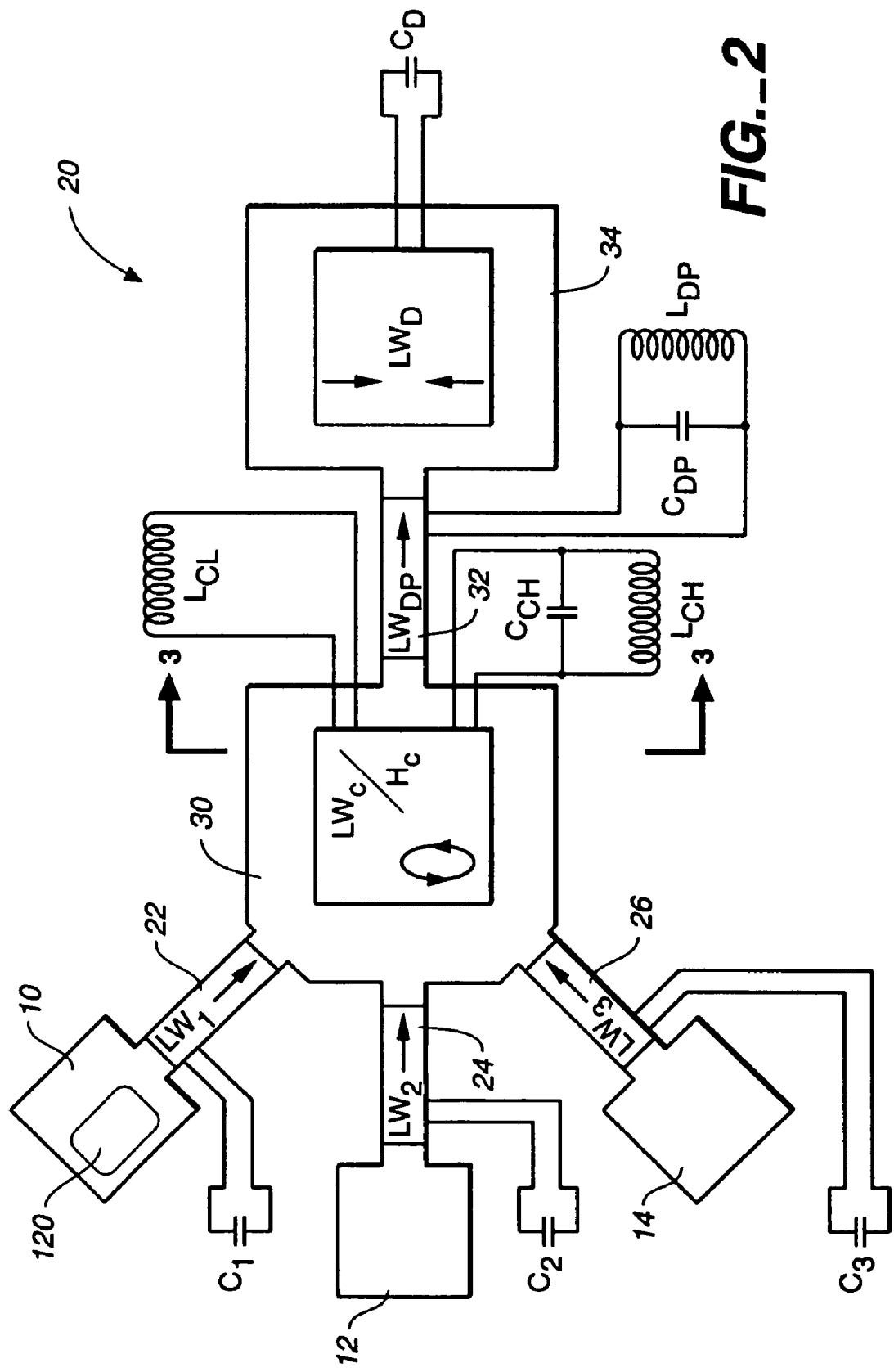
FIG._2

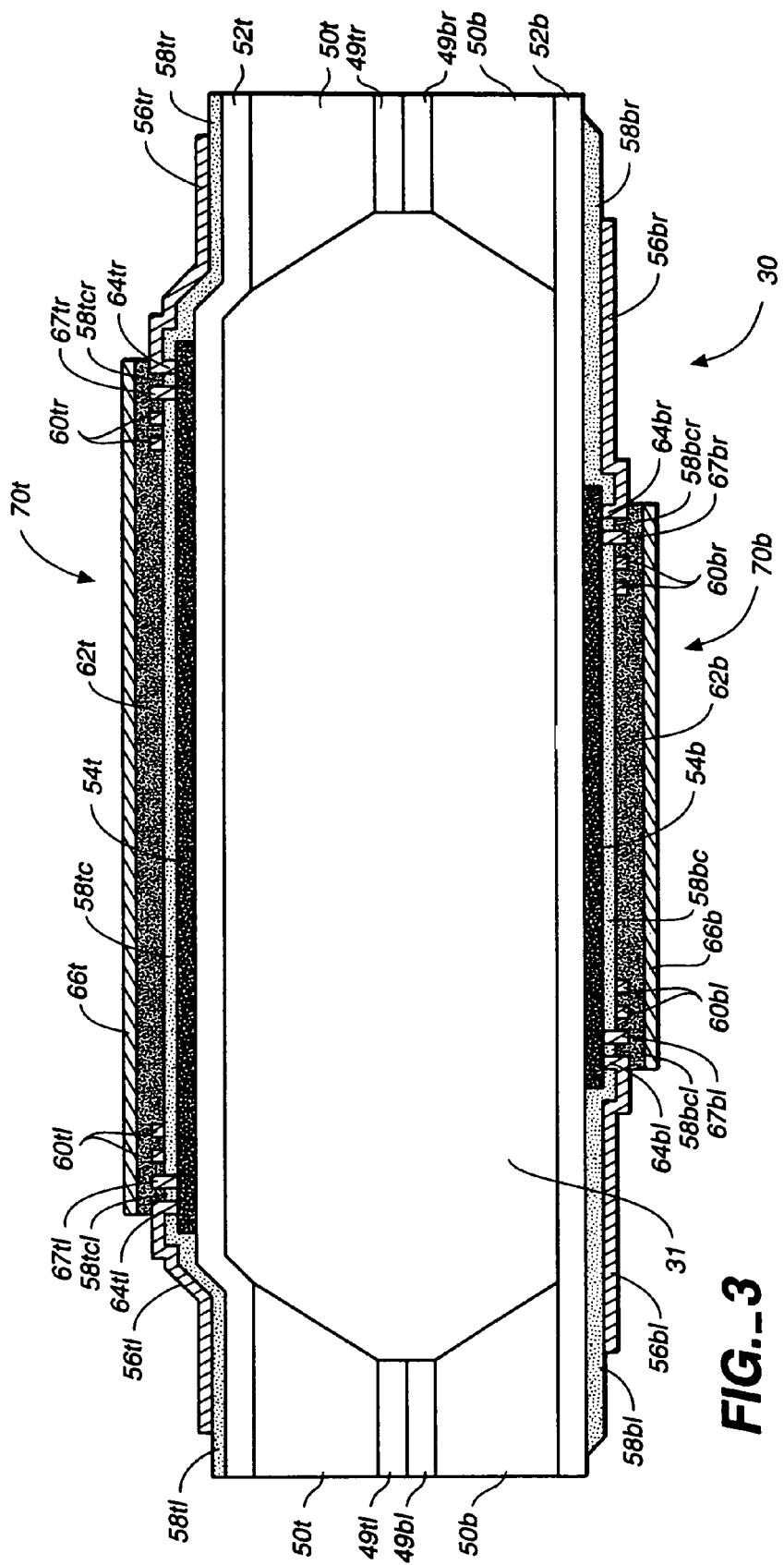
FIG._3

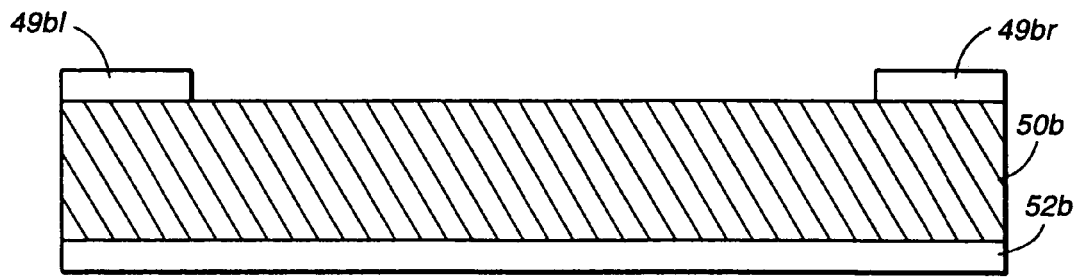
FIG._4A
FIG._4B
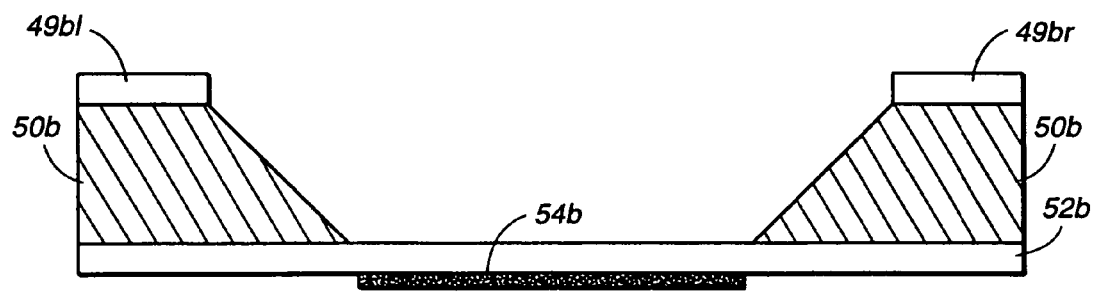
FIG._4C

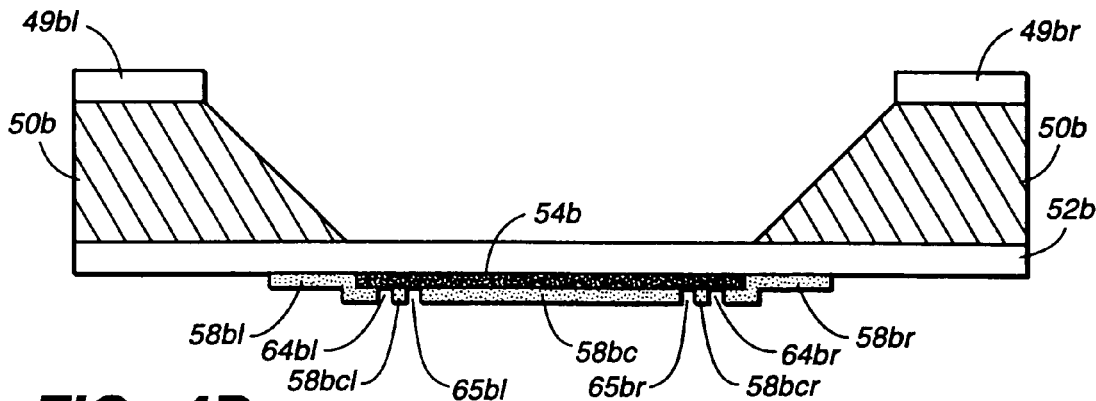
FIG._4D
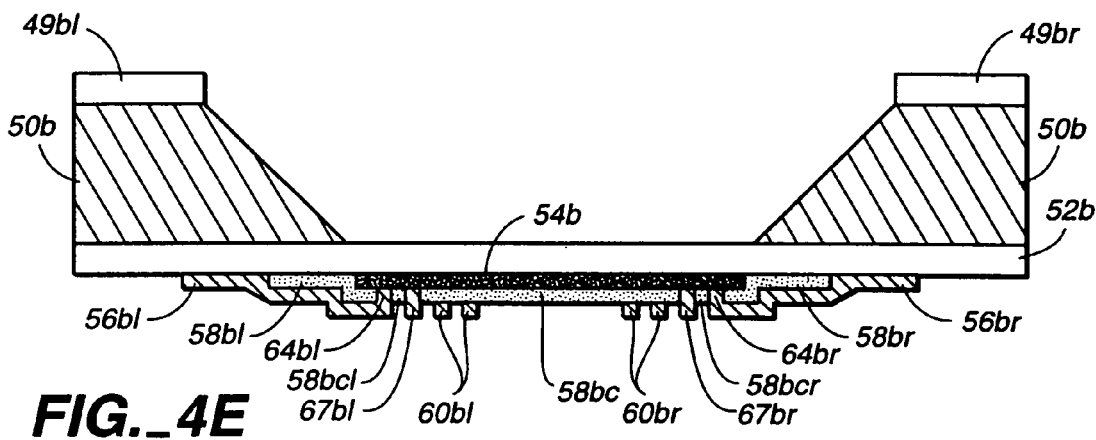
FIG._4E
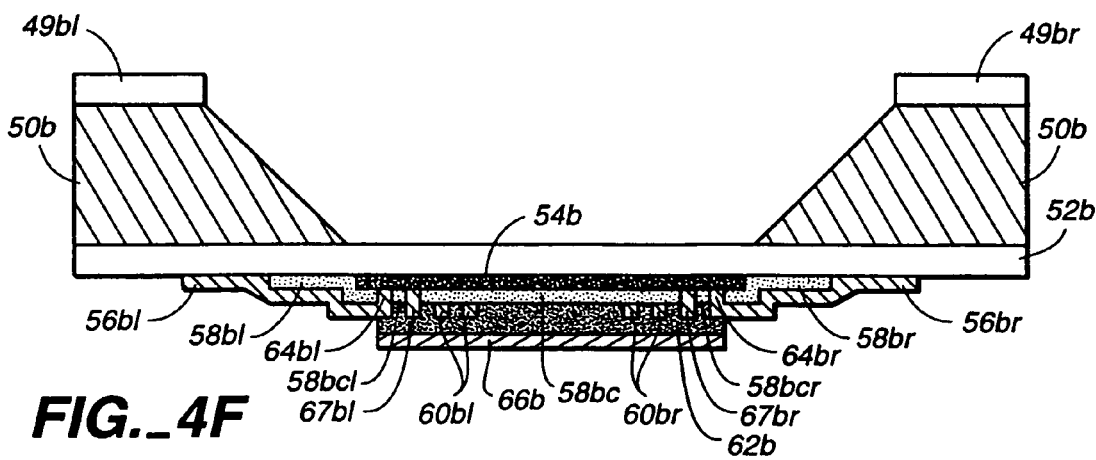
FIG._4F

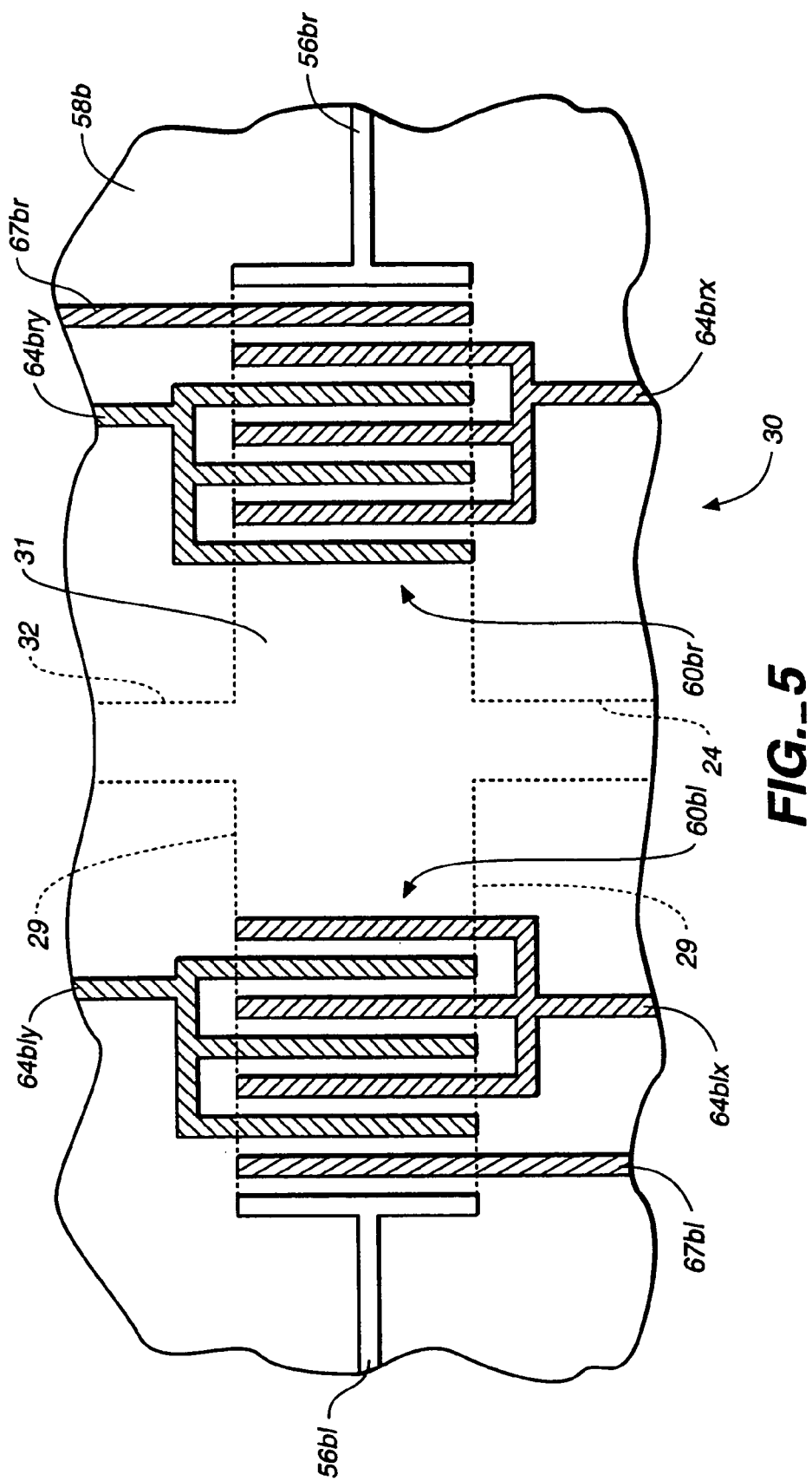
FIG._5

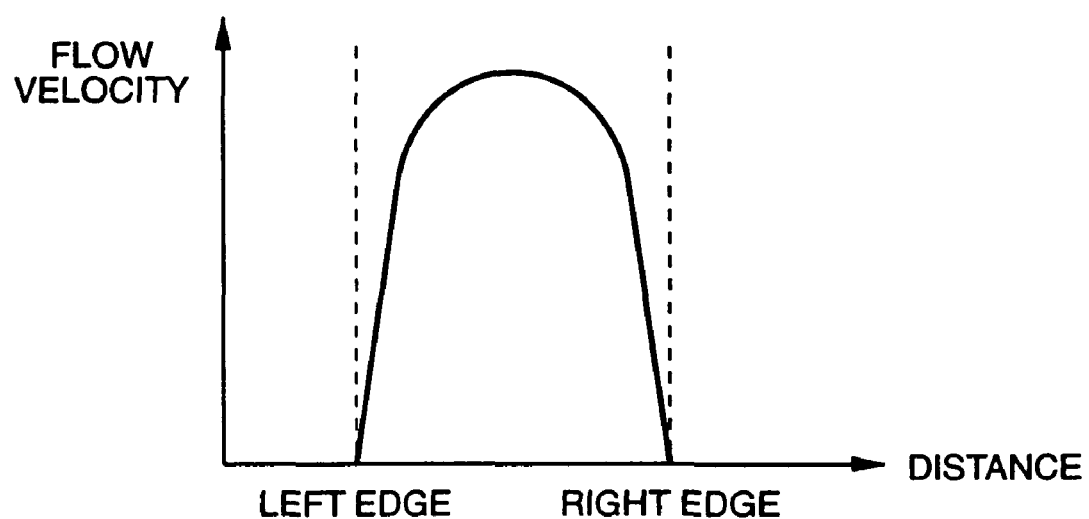
FIG._6A
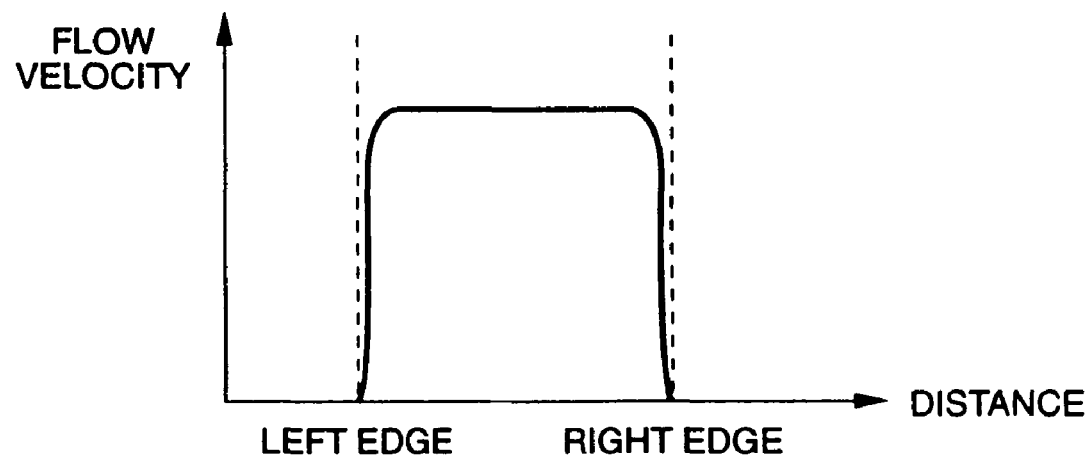
FIG._6B

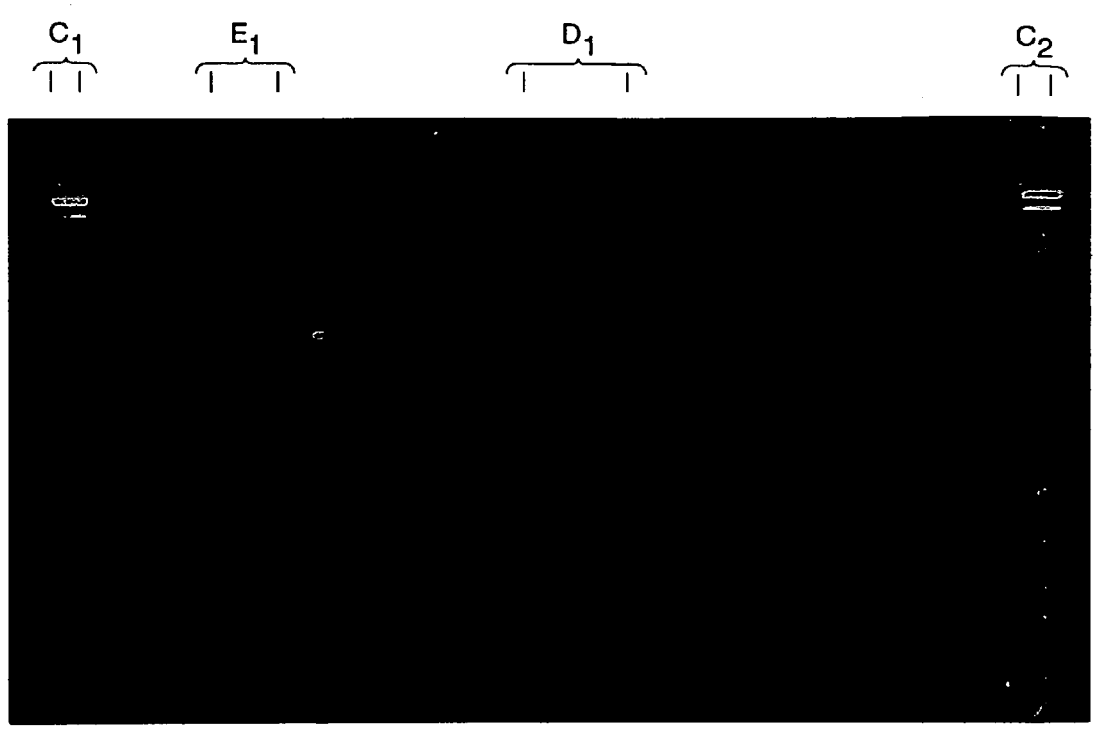
FIG._7

MICROFABRICATED REACTOR, PROCESS FOR MANUFACTURING THE REACTOR, AND METHOD OF AMPLIFICATION

RELATED APPLICATIONS

This application is a Continuation of Ser. No. 08/482,933 filed Jun. 6, 1995, now U.S. Pat. No. 7,297,313 which is a continuation of Ser. No. 07/938,106, filed Aug. 31, 1992 now U.S. Pat. No. 5,639,423 and is related to U.S. Pat. No. 5,129,261, Ser. No. 07/467,412, filed Jan. 18, 1990, issued Jul. 14 1992, and application Ser. No. 07/162,193, filed Feb. 29, 1988, now abandoned, for a Plate-mode Ultrasonic Sensor. The entire disclosures of these application are hereby incorporated by reference.

BACKGROUND OF THE INVENTION

The present invention relates generally to instruments for chemical reaction control, product and reactant manipulations, detection of participating reactants and resultant products, and more particularly to integrated microfabricated instruments which perform microscale chemical reactions involving precise control of parameters of the reactions. The parameters of the reaction controlled by the instrument may be temperature, pressure, concentration of reactants, the intensity or frequency of incident light, electromagnetic fields, or ultrasonic pressure waves, etc.

The term "integrated microfabrication" is used herein to refer to all processes used for batch production of semiconductor microelectronics, and all related microfabrication processes such as LIGA (see R. S. Muller, R. T. Howe, S. D. Senturia, R. L. Smith, and R. M. White, ed. MICROSENSORS, IEEE Press, 472 pages, 1990). Microfabrication technologies include, but are not limited to, sputtering, electrodeposition, low-pressure vapor deposition, photolithography and etching. Microfabricated devices are usually formed on crystalline semiconductor substrates such as silicon or gallium arsenide. Noncrystalline materials such as glass or certain polymers may be used although crystalline materials provide certain advantages. The shapes of crystalline devices can be precisely controlled since etched surfaces are generally crystal planes, and crystalline materials may be bonded by processes such as fusion at elevated temperatures or the field-assisted method (Mallory bonding). Materials which are not semiconductors, such as quartz or glass, may be used, though semiconductor materials provide the advantage that electronic circuitry may be integrated into the system by the use of conventional integrated-circuit fabrication techniques.

Monolithic microfabrication technology now allows the production of electrical, mechanical, electromechanical, optical, chemical and thermal devices including pumps, valves, heaters, mixers and species detectors for microliter to nanoliter quantities of solids, liquids and gases. Microscale sensors include optical waveguide probes and ultrasonic flexural-wave sensors. The integration of these devices into a single system allows for the batch production of microscale reactor-based analytical instruments. Integrated microinstruments may be applied to biochemical, inorganic, or organic chemical reactions to perform biomedical and environmental diagnostics, and biotechnological processing and detection.

Such integrated microfabricated devices can be manufactured in batch quantities with high precision, yet low cost, thereby making recyclable and/or disposable single-use devices practical. Alternatively, the instrument may consist of an array of reaction instruments which are to operate in parallel to simultaneously perform a number of related reactions. Operation of such instruments is easily automated, further reducing costs. Since the analysis can be performed in situ, the likelihood of contamination is very low. Because of the inherently small sizes of such devices, the heating and cooling can be extremely rapid, and the devices can have very low power requirements. Such devices may be powered by batteries or by electromagnetic, capacitive, inductive or optical coupling.

Small volumes and high surface-area to volume ratios provide microfabricated reaction instruments with a high level of control of the parameters of a reaction. Heaters may produce temperature cycling or ramping, sonochemical and sonophysical changes in conformational structures may be produced by ultrasound transducers, and polymerizations may be generated by incident optical radiation.

Synthesis reactions, and especially synthesis chain reactions such as the polymerase chain reaction (PCR), are particularly well-suited for microfabricated reaction instruments. PCR can selectively amplify a single molecule of DNA (or RNA) of an organism by a factor of $10^6$ to $10^9$. This well-established procedure requires the repetition of heating (denaturing) and cooling (annealing) cycles in the presence of an original DNA target molecule, specific DNA primers, deoxynucleotide triphosphates, and DNA polymerase enzymes and cofactors. Each cycle produces a doubling of the target DNA sequence, leading to an exponential accumulation of the target sequence. PCR-based technology has been applied to a variety of analyses, including environmental and industrial contaminant identification, medical and forensic diagnostics, and biological research.

The procedure involves: (1) processing of the sample to release target DNA molecules into a crude extract; (2) addition of an aqueous solution containing enzymes, buffers, deoxyribonucleotide triphosphates (dNTPS), and oligonucleotide primers; (3) thermal cycling of the reaction mixture between two or three temperatures (e.g., 90-96, 72, and 37-55° C.); and (4) detection of amplified DNA. Intermediate steps which incorporate signal-producing and/or surface-binding primers, or which purify the reaction products, via, for example, electrophoresis or chromatography may be introduced. A problem with standard PCR laboratory techniques is that the PCR reactions may be contaminated or inhibited by introduction of a single contaminant molecule of extraneous DNA, such as those from previous experiments, or other contaminants, during transfers of reagents from one vessel to another.

PCR reaction volumes are presently typically on the order of 50 microliters. A thermal cycle typically consists of heating a sample to a first temperature, maintaining the sample at the first temperature, cooling the sample to a second lower temperature, and maintaining the temperature at that lower temperature. The rate at which the sample is heated is generally limited by the heater rather than the rate of heat transfer to the sample. Presently, each of the four stages of a thermal cycle requires approximately one minute, and the time required for twenty to forty complete thermal cycles is therefore from about one to three hours. The cycling time has been reduced by performing the PCR reaction in capillary tubes (see C. T. Wittwer, G. C. Fillmore, and D. J. Garling, Analytical Biochemistry, 186, pp. 328-331 (1990)). A high-power forced air heater was used to heat the tubes. The thinnest capillary tubes contained a sample volume of about ten microliters. Each cycle consisted of a heating step, a waiting period, a cooling step and another waiting period, and each step required approximately fifteen seconds.

Although the PCR reaction requires thermal cycling of the reagents, any reaction that benefits from precise temperature control, and/or rapid thermal cycling, thermal ramping, or any other temperature variation of reagents with time (hereinafter to be referred to as temperature programming) will be well suited for the microfabricated reaction instrument of the present invention.

An object of the present invention is therefore to provide a integrated microfabricated reactor.

Another object of the present invention is to provide a reactor-based instrument for inorganic, organic and biochemical reactions, and in particular for diagnostics.

Another object of the present invention is to provide a reactor which provides high-precision control of reaction parameters.

Another object of the present invention is to provide a reactor which provides high-precision temperature control.

Another object of the present invention is to provide a reactor which provides rapid high-precision thermal cycling, ramping or programming.

Another object of the present invention is to provide a closed system reactor which is self-contained, e.g. which is shipped from the factory containing the reagents, thereby minimizing the susceptibility to contamination.

Another object of the present invention is to provide low-cost reaction and/or detection systems.

Another object of the present invention is to provide an instrument for in situ reactions which may be powered by incident electromagnetic radiation or batteries.

Another object of the present invention is to provide arrays of microfabricated reaction chambers which may operate in parallel or series.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the claims.

SUMMARY OF THE INVENTION

The present invention is directed to an instrument for in situ chemical reactions in a microfabricated environment. The instrument is especially advantageous for biochemical reactions which require high-precision thermal cycling, particularly DNA-based manipulations such as PCR, since the small dimensions typical of microinstrumentation promote rapid cycling times.

The present invention provides a reaction instrument comprised of integrated microfabricated elements including a reagent chamber and a means for manipulating the reaction of the reagents.

BRIEF DESCRIPTION OF THE DRAWINGS

The accompanying drawings, which are incorporated in and constitute a part of the specification, schematically illustrate a preferred embodiment of the invention and, together with the general description of the preferred embodiment given below, serve to explain the principles of the invention.

FIG. 1 shows a cut-away perspective view of a reaction instrument of the present invention mounted in a power source/control apparatus.

FIG. 2 is a schematic of a reaction instrument of the present invention.

FIG. 3 shows a cross-sectional view of a reaction chamber of the present invention.

FIGS. 4(a) through 4(f) show cross-sectional views of the stages of fabrication of a reaction chamber of the present invention.

FIG. 5 shows a top view of a reaction chamber (dashed outline) below the piezoelectric and ground plane layers.

FIG. 6a shows the typical flow velocity profile field for a fluid forced through a conduit with static bottom and side surfaces, and FIG. 6b shows the flow velocity profile for a fluid pumped through a conduit by a flexural-wave pump.

FIG. 7 shows gel electrophoretic results verifying the amplification of an HIV genetic sequence in a microfabricated reaction chamber of the present invention.

DESCRIPTION OF THE PREFERRED EMBODIMENT

The microinstrument of the present invention has integrated microfabricated components that perform reactant and product manipulations and detection on microliter to picoliter samples. By the selection and integration of appropriate microfabricated devices, a precise and reliable reaction and analysis instrument for PCR-based diagnostics is implemented.

The instrument may be fabricated in a wide variety of different forms. Many microinstruments may be manufactured on a single wafer and can run in parallel, allowing the processing and analysis of several target agents and controls simultaneously. Individual small and disposable dies, each a complete microinstrument, may be fabricated. The device may be fabricated to allow a continual flow of reagents through the instrument. A reagent reservoir of the microinstrument may have a thin silicone rubber wall so that the reagent may be inserted into the microinstrument by a hypodermic needle. Alternatively, a needle may be integrated into the microinstrument so that a patient can be pricked by the needle and a blood sample, or any other type of body fluid, will directly enter the instrument. An integrated needle can also be used to extract body fluids from plants and animals. The reagent may also be loaded into the microinstrument by pipetting, a modified ink-jet printing process, or other means at the factory. The reagent may be lyophilized or dried, or previously stored in the chamber.

Detection signals may be processed and stored by integrated microelectronic devices so that result interpretation and control mechanisms (which may utilize feedback) can be integrally contained on the microinstrument. The low power needs of microinstrumentation allows such systems to be powered by incident electromagnetic radiation, low voltage batteries, or incident optical radiation converted to electrical energy by on-board photocells.

The components of a microinstrument may include reservoirs for retaining reagents, agitators and mixers, heaters to perform denaturing and annealing cycles, pumps, optical and/or electromechanical sensors to discriminate reagents, and reagent separators. Microheaters may be resistive heaters consisting of materials such as polysilicon patterned onto and made an integral part of the microstructure. The micropumps may be Lamb-wave devices (see U.S. Pat. No. 5,006,749, R. M. White, 1991), electrokinetic pumps, or other microfabricated pump structures. The microdetection instruments may be fluorescence-based optical fiber spectroscopes which utilize microfabricated light sources and detectors (e.g., LEDs or diode lasers and detectors); Lamb-wave sensors (see U.S. Pat. No. 5,129,261, Ser. No. 07/467,412 filed Jan. 18, 1990, and application Ser. No. 07/775,631 filed Oct. 10, 1991); electrochemical detection of biochemical molecules by surface plasmon resonance or other processes involving immobilized biochemicals; electrochemical sensing devices; or other appropriate detection methodologies. Surface treatments may be applied to components of the device for reaction enhancement, product separation, and species detection. The surface treatments can be based on numerous well-known procedures such as silanol-based derivatizations or other appropriate treatments. Chemical species separators can utilize microelectrophoresis either in a capillary or within a gel, or can be based on other appropriate methodologies.

One embodiment of the present invention performs the polymerase chain reaction (PCR). The minute reagent volumes and the specific reaction sequence of the PCR technique play favorably into the advantages of the present invention. The integrated microsystem provides a highly automated, miniaturized, analytical instrument for very rapid in situ analyses and production of a variety of samples. Integrated microfabricated PCR instruments are capable of performing, in situ, many reactions and manipulations with precise control of temperature, evaporation, small-volume reagent delivery, product separation, isolation and detection. Such highly automated technologies should greatly expedite the use of DNA-based technologies for biomedical (e.g., the Human Genome Project); environmental (e.g., contaminant identification); industrial (e.g., biotechnology); and forensic applications. The principles applied and problems solved in developing a PCR instrument may of course be applied to other chemical reactions, analyses, and syntheses, especially other biochemical reactions, analyses, and syntheses.

PCR in a microdevice can be just one step in a series of manipulations leading to the diagnostic detection of a variety of target species or the use of PCR products in genetic engineering. Physical and chemical treatments such as those described below can also be incorporated into the pre-PCR and post-PCR phases of microdevice-based treatments to augment the reactions in situ. Amplification via PCR yields products that may be subject to further enhancement or utilized for detection of other chemicals. Physical and chemical control via microdevices of biological cells and reagents prior to and after the production of PCR products will expand the number of the potential applications of DNA-based processes and analyses.

Pre-PCR manipulation of target cells or microorganisms can be accomplished with microdevices of the present invention. For example ultrasonic waves may be applied to disrupt and expose cell components through lysis, and to unravel large or long chain molecules such as DNA and proteins via disruption of secondary structure. Cell lysis may also be induced electrically or chemically. Ultrasonic waves and surface chemistry treatments can be used to manipulate cells and cell-contents, as can chemical treatment by stirring and/or mixing reagents from other chambers on the microinstrument. Sonication on a macro-scale in conjunction with agitating microparticles, for example, has been used to facilitate the extraction of DNA from parafin-embedded fixed cells (M. J. Heller, L. J. Burgart, C. J. Ten Eyck, M. E. Anderson, T. C. Greiner, and R. A. Robinson, Biotechniques, 11, #3, 1991, pp. 372-377). Strategies similar to this which rely on the inherent properties of a microdevice can be used to process intact cells, microorganisms, tissues, and other analytical samples for PCR and subsequent techniques.

Potential post-PCR treatments by the microdevice are also numerous. It should be noted that PCR is often an integral part of the potential application of a device to further biotechnological manipulations and analyses. Once PCR has been performed, post-PCR manipulations can lead to a myriad of possible microdevice-based DNA analyses and treatments. A few examples of such analyses are: large-scale and small-scale DNA sequencing of target species, cell-typing, analysis of PCR products with DNA probes, DNA recombination, DNA fingerprinting, DNA cloning, cell cloning, physical mapping of genes, incorporation of genetic vectors, genetic therapy, treatment and testing of biotechnological processes, and the maintenance of DNA libraries. Such analyses can lead to the use of DNA as vectors to produce cells or other biological entities to make desired products such as proteins or other compounds, or it can be used to produce DNA for use in therapies or biotechnological processes.

PCR products may also be manipulated in order to be incorporated into genetic engineering vectors such as plasmids. The vectors may subsequently be incorporated into target cells for the production of desired compounds. The target cells or moieties and reagents can be stored in reservoirs on the device and released for exposure to the vectors when the proper physical/chemical conditions have been established. One other potential application would be the in situ (in vitro or in vivo) release of PCR products for direct genetic therapy or manipulations. Direct DNA sequencing of PCR products (single or double-stranded) can be accomplished with the use of unique temperature, enzymatic, or other separation schemes and detection methodologies; all of which can be incorporated into a microdevice.

Detection windows, reflective and absorptive surfaces, optic sources and other optical components can be fabricated and integrated onto a microdevice instrument, providing optical detection capabilities. The status of a reaction may be monitored by illuminating the reagents through an optical window and measuring absorption and/or luminescence. A waveguide may be fabricated by depositing a plane of transparent material between semiconducting planes, or by bonding two wafers together, at least one of the wafers having a transparent surface layer. The optical path of the waveguide is parallel to the fabrication surface. Alternatively, a window which an optical path parallel to the normal vector of the fabrication surface may be constructed using standard patterning techniques. Data analyses can be accomplished with on-board electronics which may provide electronic or optical output.

Analysis of PCR products, sequences of target DNA, or synthetic analogues in microdevices can be accomplished with the manipulative capabilities of microfabricated electrical and mechanical machines. For example, two-dimensional arrays of pre-determined DNA sequences (probes) can be used to detect or verify PCR products, and their subsequent analyses can be accomplished with microdevices.

As shown in FIG. 1, an embodiment 20 of the present invention is shown above a recess 105 in a power source/control system 100. A hypodermic need 110 is shown inserting a sample through a silicone rubber window 120 into a reaction instrument 20. The reaction is controlled and powered by: inductive coupling, such as that between coil $L_{CL}$ in the instrument 20 and a magnetic coil 130 as shown in FIG. 2; by capacitive coupling, such as that between the plates of capacitor $C_3$ and plates 140a and 140b; and by electromagnetic coupling between resonant circuit (not shown) in the instrument 20 and a radio-frequency antenna 135.

A schematic of a preferred embodiment 20 of the present invention is shown in FIG. 2. Three reagent chambers 10, 12 and 14 contain reactants. One chamber 10 contains the DNA primers, one chamber 12 contains the polymerase, and one chamber 14 contains the nucleotides and any detection-tag molecules, such as magnetic beads. The contents of the chambers 10, 12 and 14 have been loaded at the factory. The target DNA molecule is placed in reagent chamber 10 by insertion of a hypodermic needle or the like through silicone rubber window 120. The window 120 may alternatively be composed of any other type of appropriate natural or synthetic elastomer. The reactants in the reagent chambers 10, 12 and 14 are connected by channels 22, 24 and 26 to a reaction chamber 30. Typically the chambers 10, 12, 14 and 30 have a volume ranging from microliters to nanoliters. The channels 22, 24 and 26 are equipped with Lamb-wave pumps $LW_1$, $LW_2$ and $LW_3$, respectively, for pumping the reactants in the reactant chambers 10, 12 and 14 in the directions of the arrows to the reaction chamber 30. The Lamb-wave pumps may be located on any wall, or on multiple walls, of the channels 22, 24 and 26. Lamb-wave pump $LW_1$ is connected to a capacitor $C_1$. Similarly the other two Lamb-wave pumps $LW_2$ and $LW_3$ are connected to capacitors $C_2$ and $C_3$, respectively.

The surface tension across the narrow midsections of the channels 22, 24 and 26 prevents the reactants from flowing into the reaction chamber 30 until pumping is initiated. The surfaces of the channels 22, 24 and 26 may be treated to raise the surface tension thereby further inhibiting flow of reagents when the pumps $LW_1$, $LW_2$ and $LW_3$ are not activated.

The reaction chamber 30 may be equipped with a Lamb-wave transducer $LW_C$ and a heater $H_C$. The Lamb-wave transducer is connected to inductor $L_{CL}$. The heater $H_C$ is connected to a resonant circuit consisting of an inductor $L_{CH}$ and a capacitor $C_{CH}$. The Lamb-wave transducer $LW_C$ acts as an agitator, mixer, or sonochemical inducer.

A channel 32 connects the reaction chamber 30 to a detection chamber 34. The channel 34 is equipped with a Lamb-wave pump $LW_{DP}$, which is connected to a resonant circuit consisting of an inductor $L_{DP}$ and a capacitor $C_{DP}$. The detection chamber 34 is equipped with a Lamb-wave sensor $LW_D$. The Lamb-wave sensor $LW_D$ is connected to a capacitor $C_D$.

For ease of notation, an exemplary Lamb-wave device chosen from the set $LW_1$, $LW_2$, $LW_3$, $LW_C$, $LW_{DP}$, and $LW_D$ will be denoted by LW and the corresponding capacitor and/or inductor electrically connected to the Lamb-wave device will be denoted by C and L, respectively, hereinafter. Lamb-wave transducers have high mechanical Q values and can therefore be powered by only a narrow range of alternating voltage frequencies. The Lamb-wave pumps $LW_1$, $LW_2$, and $LW_3$, and the Lamb-wave sensor $LW_D$ are powered capacitively by generating an electric field between the plates 140a and 140b at the resonant frequencies of the Lamb-wave transducers $LW_1$, $LW_2$, $LW_3$, and $LW_D$. The alternating frequency electric fields generate alternating frequency voltages across the capacitors $C_1$, $C_2$, $C_3$ and $C_D$, and Lamb waves at this frequency in the transducers $LW_1$, $LW_2$, $LW_3$ and $LW_D$. But because the transducers $LW_1$, $LW_2$, $LW_3$, and $LW_D$ have high Q values, only when the frequency of the imposed field is near the resonant frequency of a transducer does the transducer vibrate with any substantial magnitude. Similarly, the Lamb-wave mixing chamber transducer $LW_C$ is powered by an alternating frequency magnetic field generated by the coil 130 at the mechanical resonant frequency of the transducer $LW_C$. The heater $H_C$ and the Lamb-wave pump $LW_{DP}$ are activated by directing an electromagnetic wave from the antenna 135 to the resonant circuits $C_{CH}$ and $L_{CH}$, and $C_{DP}$ and $L_{DP}$, respectively. The frequency of the incident electromagnetic radiation must correspond to the resonant frequency of the electrical elements $C_{DP}$, $L_{DP}$ and $LW_{DP}$, and must also correspond to the mechanical resonant frequency of the transducer $LW_{DP}$, to activate the pump $LW_{DP}$. The frequency of the incident electromagnetic radiation must correspond to the resonant frequency of the electrical elements $C_H$, $L_{CH}$ and $H_C$ to activate the heater $H_C$.

The PCR reaction is initiated by pumping the reagents in the reagent chambers 10, 12 and 14 along the directions of the arrows to the reaction chamber 30 by activating the reagent pumps $LW_1$, $LW_2$ and $LW_3$. A series of approximately twenty to forty thermal cycles are then initiated, during each cycle the temperature of the reactants in the reaction chamber 30 goes from 55° C. to 96° C., and back to 55° C., for example. The temperature of the reaction chamber 30 is determined by the power of the incident electromagnetic signal at the frequency corresponding to the resonant frequency of the circuit comprised of the capacitor $C_{CH}$, and the inductor $L_{CH}$, together with the heater $H_C$. The reaction chamber 30 Lamb-wave device $LW_C$ acts as an agitator or mixer as described below to mix the reagents and promote the reaction.

When the thermal cycling is complete the contents of the reaction chamber 30 are pumped by Lamb-wave pump $LW_{DP}$ in the direction of the arrow to the detection chamber 34. The preferred embodiment utilizes a Lamb-wave sensor $LW_D$. Alternatively, the detection chamber may be provided with an optical window and testing may be performed by fluorescence-based or absorption-based optical spectroscopy.

A cross-sectional view taken along line 3-3 of FIG. 2 of the reaction chamber 30 is shown in FIG. 3. FIGS. 4(a)-(f) show cross-sectional views of the bottom half of the chamber during successive stages of formation of the chamber 30 from a silicon substrate 50b. A similar set of stages are involved in the fabrication of the top portion of the chamber 30. Once fabricated, the top and bottom portions may be bonded together by Mallory bonding.

The chamber cavity 31 is bounded by a ceiling 70t, a floor 70b, and side walls consisting of silicon sections 50t and 50b and silicon nitride sections 49tl, 49bl, 49tr and 49br. The height of the chamber cavity 31 is approximately 0.5 mm, and the width and length of the chamber are approximately 4 mm or less. The whole instrument 20 may fit on a wafer as small as 1 cm×1 cm×0.5 cm.

The indentations in the silicon substrates 50b and 50t are formed by coating one side of the substrates 50b and 50t with silicon nitride layers 52b and 52t, and patterning silicon nitride layers on the other sides of the substrates 50b and 50t to form sections 49bl, 49br, 49tl, and 49tr, respectively, as shown in FIGS. 3 and 4(a). The silicon-nitride layers 52t and 52b are preferably applied by low-pressure chemical-vapor deposition of the silicon-nitride, and are preferably a low-stress nitride. The thickness of silicon-nitride layers 52t and 52b is chosen to provide a balance between the mechanical strength of the layers which increases with thickness, and the sensitivity of the Lamb-wave detector which decreases with thickness. The thickness is also chosen to provide practical resonant frequencies for the device. The thickness of the silicon-nitride layers 52t and 52b is preferably about 3 μm, plus or minus ten percent.

The system is etched, for example with the wet chemical etchant KOH, to create a cavity in the silicon substrate 50 as shown in FIG. 4(b). The remaining sections of silicon 50bl and 50br form portions of the side walls of the cavity 31.

Located outside the reaction chamber cavity 31 to the exterior of nitride layers 52b and 52t are top and bottom polycrystalline silicon layers 54t and 54b, respectively. The polycrystalline layers 54t and 54b are deposited on the nitride layers 52b and 52t by chemical vapor deposition and selectively patterned. The bottom portion of the chamber 30 with the patterned polycrystalline layer 54b on the silicon nitride layer 52b is shown in FIG. 4(c). The thickness of the polycrystalline layers 54t and 54b is preferably between 2000 and 4000 angstroms, and more preferably 3000 angstroms, plus or minus five percent.

Top and bottom barrier layers, composed of an insulating material such as low-stress silicon nitride or silicon dioxide, are deposited by low-temperature oxidation and patterned. The lower barrier layers 58$bl$, 58$bcl$, 58$bc$, 58$bcr$ and 58$br$ lie to the exterior of the polycrystalline layer 54$b$ and the nitride layer 52$b$ as shown in FIG. 4($d$). Similarly, the upper barrier layers 58$tl$, 58$tcl$, 58$tc$, 58$tcr$, and 58$tr$ lie to the exterior of the polycrystalline layer 54$t$ and the nitride layer 52$t$. Left and right top access holes 64$tl$, 64$tr$, 65$tl$, and 65$tr$ provide access to the polycrystalline layer 54$t$. Similarly, left and right bottom access holes 64$bl$, 64$br$, 65$bl$, and 65$br$ provide access to the bottom polycrystalline layer 54$b$. The thickness of the barrier layers 58$tl$, 58$tcl$, 58$tc$, 58$tcr$, and 58$tr$, (to be collectively referred to as 58$t$) and 58$bl$, 58$bcl$, 58$bc$, 58bcr and 58$br$ (to be collectively referred to as 58$b$) is preferably between 1000 and 5000 angstroms, and more preferably 2500 angstroms, plus or minus ten percent. The nitride layers 52$b$ and 52$t$ and the barrier layers 58$b$ and 58$t$ thermally isolate the polycrystalline layers 54$b$ and 54$t$ from the high conductivity silicon layers 50$bl$, 50$br$, 50$tl$ and 50$tr$, thereby increasing the effectiveness of the heaters formed by the polycrystalline layers 54$b$ and 54$t$.

As shown in FIGS. 3 and 4($e$), top left and right conducting leads 56$tl$ and 56$tr$, bottom left and right conducting leads 56$bl$ and 56$br$, top left and right transducers 60$tl$ and 60$tr$, bottom left and right transducers 60$bl$ and 60$br$, top left and right four-contact resistance monitoring leads 67$tl$ and 67$tr$, and bottom left and right four-contact resistance monitoring leads 67$bl$ and 67$br$ are then patterned onto the device. Through access holes 64$tl$ and 64$tr$, the leads 56$tl$ and 56$tr$ make electrical contact with the polycrystalline layer 54$t$, and similarly for the bottom section of the chamber 30. Through access holes 65$tl$ and 65$tr$, the leads 67$tl$ and 67$tr$ make electrical contact with the polycrystalline layer 54$t$, and similarly for the bottom section of the chamber 30. The top polycrystalline layer 54$t$ is therefore electrically connected to leads 56$tl$, 56$tr$, 67$tl$ and 67$tr$. Similarly, the bottom polycrystalline layer 54$b$ is electrically connected to lead 56$bl$, 56$br$, 67$bl$ and 67$br$. Current passing through polycrystalline layers 54$t$ and 54$b$ generates heat. Therefore, the temperature of the chamber 30 can be controlled by the amount of voltage applied across the top and bottom leads 56$tl$ and 56$tr$, and 56$bl$ and 56$br$, respectively. Because the exterior temperature is generally below that of the chemical reactions the system is cooled by the ambient air and cooling elements are not generally required.

The temperature of the system is monitored by measurement of the resistance of the polycrystalline layers 54$t$ and 54$b$ by connecting leads 67$tl$ and 67$tr$, and 67$bl$ and 67$br$ of four-contact resistance measuring circuits (not shown) to the top and bottom polycrystalline layers 54$t$ and 54$b$, respectively. The resistance increases linearly with temperature.

FIG. 5 depicts a view of the bottom of the chamber 30 subsequent to the deposition of the transducers 60$bl$ and 60$br$, leads 56$bl$ and 56$br$, and four-contact resistance leads 67$bl$ and 67$br$, as shown in FIG; 4($e$). For clarity not all transducer leads 64$blx$, 64$bly$, 64$brx$ and 64$bry$ shown in FIG. 5 are depicted in FIGS. 3, 4($e$) and 4($f$). Only six fingers per transducer 60$tl$ and 60$tr$ are shown in FIG. 5 for clarity, though transducers having approximately twenty or more fingers are preferred. The cavity 31 and channels 24 and 32 lay beneath the barrier layer 58$b$ in the region between the dashed lines 29 and the crossbars of the T-shaped leads 56$bl$ and 56$br$. The access holes 64$bl$ and 64$br$ (not shown in FIG. 5) lie beneath the cross-bars of the leads 56$bl$ and 56$br$, and the access holes 65$bl$ and 65$br$ (not shown in FIG. 5) lie beneath the cross-bars of the leads 67$bl$ and 67$br$, respectively. The bottom left Lamb-wave transducer 60$bl$ consists of a plurality of interlaced fingers which are electrically connected to a pair of transducer leads 64$blx$ and 64$bly$. The top left and right transducers 60$tl$ and 60$tr$ and the bottom left and right transducers 60$bl$ and 60$br$ have similar shapes. The bottom transducers 60$bl$ and 60$br$ and the bottom transducer leads 64$bly$, 64$blx$, 64$bry$ and 64$brx$, and the leads 56$bl$, 56$br$, 67$bl$ and 67$br$ are aluminum and have a thickness of preferably 2000 to 6000 angstroms, and more preferably a thickness of 4000 angstroms, plus or minus ten percent. The bottom transducers 60$bl$ and 60$br$ and leads 56$bl$, 56$br$, 67$bl$, and 67$br$ may be alternatively be made of low-temperature oxide, or any other appropriate conducting material. The top transducers 60$tl$ and 60$tr$ and leads 56$tl$, 56$tr$, 67$tl$, and 67$tr$ may be similarly constructed.

As shown in FIGS. 3 and 4($f$), a bottom piezoelectric layer 62$b$ extending between and covering leads 67$bl$ and 67$br$, fingers of the bottom transducers 60$bl$ and 60$br$, and portions of leads 56$bl$ and 56$br$ is then deposited and patterned. Similarly, a top piezoelectric layer 62$t$ extending between and covering leads 67$tl$ and 67$tr$, fingers of the bottom transducers 60$tl$ and 60$tr$, and portions of leads 56$tl$ and 56$tr$ is then deposited and patterned. The piezoelectric material may be ZnO or any other appropriate material. The thickness of the piezoelectric sections 62$t$ and 62$b$ is preferably between 0.5 and 2.0 μm, more preferably 1 μm, plus or minus ten percent.

The piezoelectric sections 62$t$ and 62$b$ are covered by top and bottom conducting ground planes 66$t$ and 66$b$, respectively, as shown in FIGS. 3 and 4($f$). The ground planes 66$t$ and 66$b$ may be aluminum, or any other appropriate conducting material. The thickness of the conducting ground plane layers 66$t$ and 66$b$ is preferably between 2000 and 6000 angstroms, and more preferably 4000 angstroms, plus or minus ten percent.

Lamb waves, also known as plate-mode waves, have a compressional component and a shear component. Together the components of a traveling Lamb-wave in a slab can transport liquids and gases adjacent the slab, much the same way ocean waves transport a surfing board. Lamb-wave devices can therefore act as pumps. Material near the surface of the slab has the maximum velocity since there are essentially no boundary layer effects. This is extremely advantageous for the small geometries associated with microdevices. FIG. 6$a$ shows the typical flow velocity of a fluid through a conduit with two planar walls to illustrate the effect of the friction induced by walls on the flow. The velocity profile is parabolic, and at the left and right edges of the conduit the velocity drops to zero due to friction between the fluid and the walls. The friction between the walls and the fluid reduces the efficiency of the pumping. In contrast, FIG. 6$b$ shows the flow velocity of a fluid through the same conduit when the front and back walls are Lamb-wave pumps. The flow velocity is almost constant between the right and left walls. The viscosity of the fluid transmits the momentum of the fluid near the Lamb-wave pumps to the fluid farther from the pumps.

Lamb waves require a propagation medium which is at most several wavelengths thick. The Lamb waves in this invention have frequencies in the approximate range of 1 to 200 MHz, and typical pumping velocities for a Lamb-wave device operated with a 10 volt transducer voltage are 300 μm/sec for water, and 2 cm/sec for air.

The layers 54$t$, 58$t$, 62$t$ and 66$t$ which border the top of the chamber cavity 31 will hereinafter be referred to as the ceiling 70$t$ of the chamber 30, and the layers 54$b$, 58$b$, 62$b$ and 66$b$ which border the bottom of the chamber cavity 31 will hereinafter be referred to as the floor 70$b$ of the chamber 30. Lamb waves are generated in the ceiling 70$t$ of the chamber 30 by applying an alternating voltage between a transducer lead, for instance the upper left lead 64tly of FIG. 5, and the top ground plane 66t. The transducer electrodes 60tly differentially deform the piezoelectric material 62t to produce a mechanical wave motion in the ceiling 70t. The amplitude of the Lamb waves is increased by applying a second alternating voltage which is 180° out of phase to the transducer lead 64tlx connected to the set of interlaced fingers.

Traveling waves are generated in the Lamb-wave pumps $LW_1$, $LW_2$, $LW_3$, and $LW_{DP}$ in the directions of the arrows of FIG. 2 by application of alternating voltages to the pumps $LW_1$, $LW_2$, $LW_3$, and $LW_{DP}$ at the arrow-tail side. Standing waves are generated in the Lamb-wave detector $LW_D$ by application of in-phase alternating voltages electrodes at both sides of the chamber. By sending Lamb-waves from left to right across the ceiling 70t of the mixing chamber 30 (by application of an alternating voltage between top left transducer 60tl and the top ground plate 66t) and Lamb waves from right to left across the floor 70b of the chamber 30 (by application of an alternating voltage between bottom right transducer 60br and the bottom ground plate 66b), a stirring or circulating action can be produced.

The phenomenon responsible for the operation of the Lamb-wave sensor $LW_D$ in the detection chamber 34 is elastic wave propagation along a medium whose characteristics can be altered by a measurand, such as viscosity or density of the ambient fluid or gas. Where the characteristics of the waves propagating along the medium are dependent upon the characteristics of the propagation medium, the wave characteristics can be monitored or measured to provide an indication of the measurand value. For example, when the device absorbs vapors or gases from the atmosphere in a film deposited on the surface, the output frequency changes. Tests and analysis indicate that Lamb-wave sensors are at least an order of magnitude more sensitive than other types of acoustical vapor sensors operating at the same wavelength. The type of DNA in an ambient fluid can be determined by measuring the viscosity as a function of temperature, since the denaturing temperatures of different types of DNA are well known.

Since Lamb-wave sensors can operate while in contact with a liquid such as water, their use as biosensors is very significant. For instance, the surface of a Lamb-wave sensor may be coated with single strands of a particular DNA molecule. If the device is immersed in a solution containing that same type of DNA molecule, the molecules in solution will pair with the molecules on the surface, increasing the mass of the membrane and therefore decreasing the frequency of oscillation. Also, the membrane may be made of a porous and permeable material, allowing the coating of a greater surface area and also allowing the liquid to be flowed through the membrane, in order to speed up the DNA attachment. Intercalating dyes, such as ethidium bromide, may be used to augment viscosity changes which occur during a reaction, thereby increasing the sensitivity of the sensor. Other biological interactions may also be sensed.

FIG. 7 shows gel electrophoresis results verifying the amplification of a specific HIV nucleic acid sequence performed by the microfabricated reaction instrument of the present invention. The two outside bands $C_1$ and $C_2$ represent calibrating size standards, and the three bands labelled as $D_1$ represent the DNA amplified in the microreactor. The two bands $E_1$ to the left of center are results obtained with a commercial PCR thermocycler instrument from the same reaction mixture as that in the microreactor. Since bands $E_1$ and $D_1$ are at the same height it is indicated that the microreactor has produced the correct target. The thermal cycles of the commercial instrument were 4 minutes long. Those of the microreactor of the present invention were 1 minute in length.

In summary, an apparatus and method for in situ chemical reactions in a microfabricated instrument has been described. It has been shown that the instrument facilitates extremely rapid thermal cycling and high-precision temperature control of microliter to nanoliter volumes. The apparatus and method are well suited for DNA-based reactions, such as PCR. It has also been shown that such integrated devices minimize the possibility for contamination of the reactions and may be operated at a distance by electromagnetic fields.

The present invention has been described in terms of a preferred embodiment. However, the invention is not limited to the embodiment depicted and described. Many variations within the scope of the present invention are possible. For instance, the instrument may consist of a series of chambers at different temperatures, and the temperature programming of the reagents may be accomplished by transport of the reagents through the series of chambers. The instrument may have an input channel and an output channel, and may be adapted to provide a continual flow-through synthesis. Thermal cycling may be accomplished by repeated transfer of reagents between two or more chambers which are heated to different temperatures.

In another alternate embodiment the monitoring of the temperature of a chamber is accomplished at a distance by connecting an LC circuit to a probe across a polycrystalline heating layer and measuring the Q-factor of the circuit. The Q-factor is measured by exciting the circuit with an incident electromagnetic field at the resonant frequency of the circuit and monitoring the time decay of the resonance, or by measuring the bandwidth of the circuit by applying a frequency modulated incident EM field and measuring the circuit's frequency response. Since the measured Q-factor is inversely proportional to the resistance and the resistance increases linearly with temperature, the temperature may be determined by the measured Q-factor.

Other possible variations within the spirit of the invention include: the dimensions of components of the instrument are not limited to those disclosed; more or fewer reactants may be used and the reactants may be organic, inorganic, or a combination of organic and inorganic; the detection means may be located in the same chamber as the mixing means; components of the device may be made of semiconducting materials other than silicon, or of quartz, glass, polymers or other materials; the microfabricated instrument may be formed by the bonding of two wafers; the instrument may be provided with optical windows for optical monitoring of the reaction; the instrument may be controlled by direct electrical coupling of control circuitry to the leads of the pumps, heater and sensor; a silicone-rubber window may form a penetrable wall of any chamber or channel; the instrument may be fabricated from a silicon-based material; the instrument may be powered by an integrated microfabricated battery; any Lamb-wave transducer may be activated by capacitive, inductive, electromagnetic or optical means; or electrokinetic pumps, or any other appropriate type of pumping means, may be substituted for the Lamb-wave pumps.

Accordingly, the scope of the invention is defined by the appended claims.

What is claimed is:
1. A device for amplifying a preselected polynucleotide in a sample of cells by conducting a polynucleotide amplification reaction, the device comprising:
    a solid substrate which is microfabricated to define:
        a sample inlet port;

a flow system for micro- to picoliter volumes, comprising:
   a sample flow channel extending from said inlet port; and
   a polynucleotide amplification reaction chamber in fluid communication with said flow channel; said chamber and said channel being of dissimilar dimension; and
a fluid exit port in fluid communication with said flow system;
an integrated component for inducing cell lysis, and
means for thermally cycling the contents of said chamber whereby in each cycle the temperature is controlled to dehybridize double stranded polynucleotide and to permit the in- vitro amplification of a preselected polynucleotide.

2. The device of claim 1, wherein said amplification reaction is a polymerase chain reaction (PCR), and wherein said amplification chamber contains: a preselected polynucleotide from said cells, a polymerase, nucleoside triphosphates, a first primer hybridizable with single strand of said polynucleotide, and second primer hybridizable with a nucleic acid comprising a sequence complementary to said single strand, wherein said first and second primers define the termini of the polynucleotide product of the polymerization reaction; and
   wherein said means for thermally cycling comprises means for thermally cycling the contents of said chamber between a temperature controlled to dehybridize double stranded polynucleotide thereby to produce single stranded polynucleotide, to permit annealing of said primers to complementary regions of single stranded polynucleotide, and to permit synthesis of polynucleotide between said primers, thereby to amplify said preselected polynucleotide.

3. The device of claim 1, wherein said cells are microorganisms.

4. The device of claim 1, wherein said solid substrate comprises microfabricated silicon.

5. The device of claim 1, wherein said integrated component is a sonicator.

6. The device of claim 1, wherein said integrated component provides a means for chemical lysis.

7. The device of claim 1, wherein said integrated component provides a means for electrical lysis.

8. The device of claim 1, wherein said cells are lysed prior to introduction into said polynucleotide amplification reaction chamber.

9. The device of claim 1, wherein said cells are lysed in said polynucleotide amplification reaction chamber.

10. A method for amplifying a preselected polynucleotide in a sample of cells by conducting a polynucleotide amplification reaction, the method comprising:
(i) providing a device comprising: a solid substrate microfabricated to define:
a sample inlet port;
a flow system for micro- to picoliter volumes comprising:
   a sample flow channel extending from said inlet port; and
   a polynucleotide amplification reaction chamber in fluid communication with said flow channel; said chamber and said channel being of dissimilar dimension; and
   a fluid exit port in fluid communication with said flow system; and
means for thermally regulating the contents of said chamber at a temperature controlled to permit amplification of said preselected polynucleotide;
(ii) delivering, through said inlet port and said flow system to said reaction chamber, a sample of cells and reagents required for an in vitro polynucleotide amplification reaction; and
(iii) thermally controlling the contents of said chamber to permit amplification of said polynucleotide.

11. The method of claim 10, wherein said cells are microorganisms.

12. The method of claim 10, wherein said amplification reaction is a polymerase chain reaction (PCR);
   wherein in step (i), said means for thermally controlling comprises means for thermally cycling the contents of said chamber;
   wherein step (ii) includes the step of adding to said amplification chamber: a polymerase, nucleoside triphosphates, a first primer hybridizable with said sample polynucleotide, and a second primer hybridizable with a nucleic acid comprising a sequence complementary to said polynucleotide, and wherein said first and second primers define the termini of the polynucleotide product of the polymerization reaction; and
   wherein step (iii) includes the step of thermally cycling the contents of said chamber whereby, in each cycle, the temperature is controlled to dehybridize double stranded polynucleotide thereby to produce single stranded polynucleotide, to permit annealing of complementary regions of single stranded polynucleotide, and to permit synthesis and polymerization of polynucleotide between said primers.

13. The method of claim 10, further comprising providing an integrated component to lyse the cells.

14. The method of claim 10, wherein said integrated component is a sonicator.

15. The method of claim 10, wherein said integrated component provides a means for chemical lysis.

16. The method of claim 10, wherein said integrated component provides a means for electrical lysis.

17. The method of claim 10, wherein said cells are lysed prior to introduction into said polynucleotide amplification reaction chamber.

18. The method of claim 10, wherein said cells are lysed in said polynucleotide amplification reaction chamber.

* * * * *